(12) United States Patent
Tang et al.

(10) Patent No.: US 11,192,882 B2
(45) Date of Patent: Dec. 7, 2021

(54) CRYSTAL FORM OF SMALL MOLECULE IMMUNE COMPOUND, PREPARATION METHOD THEREOF AND PHARMACEUTICAL COMPOSITION CONTAINING THE SAME

(71) Applicant: SHENZHEN NEPTUNUS PHARMACEUTICAL RESEARCH INSTITUTE CO., LTD., Guangdong (CN)

(72) Inventors: Tian Tang, Guangdong (CN); Zhiying Huang, Guangdong (CN); Jing Wu, Guangdong (CN); Yanping Chen, Guangdong (CN); Tao Shi, Guangdong (CN); Yanqing Wang, Guangdong (CN); Jing'an Yang, Guangdong (CN)

(73) Assignee: Shenzhen Neptunus Pharmaceutical Research Institute Co., Ltd.

( * ) Notice: Subject to any disclaimer, the term of this patent is extended or adjusted under 35 U.S.C. 154(b) by 0 days.

(21) Appl. No.: 16/966,419

(22) PCT Filed: Jan. 31, 2019

(86) PCT No.: PCT/CN2019/074248
§ 371 (c)(1),
(2) Date: Jul. 30, 2020

(87) PCT Pub. No.: WO2019/149254
PCT Pub. Date: Aug. 8, 2019

(65) Prior Publication Data
US 2021/0032223 A1    Feb. 4, 2021

(30) Foreign Application Priority Data

Feb. 1, 2018   (CN) .......................... 201810100519.5

(51) Int. Cl.
*C07D 403/06*    (2006.01)

(52) U.S. Cl.
CPC ........ *C07D 403/06* (2013.01); *C07B 2200/13* (2013.01)

(58) Field of Classification Search
CPC combination set(s) only.
See application file for complete search history.

*Primary Examiner* — Heidi Reese
(74) *Attorney, Agent, or Firm* — Thorpe North & Western, LLP.

(57) ABSTRACT

Provided in the present invention are a crystal form of a small molecule immune compound, a preparation method therefor and a pharmaceutical composition containing the same; the compound is (3Z,6Z)-3-[((E)-3-(5-tert-butyl)-1H-imidazolyl-4-yl)methylene]-6-((E)-3-(3-fluorophenyl)-2-propenylene)piperazine-2,5-dione; the crystal form thereof has stable morphology, good chemical stability, high temperature resistance, and is used for treating hyperproliferative diseases. The structural formula of the compound is as shown in formula (I).

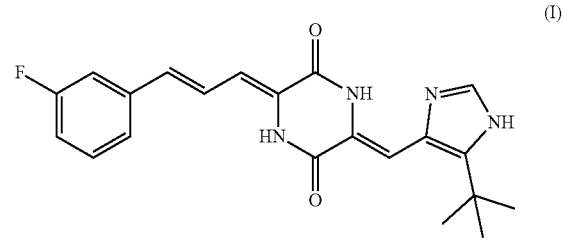

(I)

8 Claims, 3 Drawing Sheets

CRYSTAL FORM OF SMALL MOLECULE IMMUNE COMPOUND, PREPARATION METHOD THEREOF AND PHARMACEUTICAL COMPOSITION CONTAINING THE SAME

FIELD OF THE INVENTION

The invention belongs to the technical field of medicine, and specifically relates to a new crystal form of a novel small molecule immune compound;

The invention also relates to the preparation method of the above new crystal form and the pharmaceutical composition containing the new crystal form of the compound.

BACKGROUND OF THE INVENTION

As the main means of tumor treatment, anti-tumor drugs have made considerable contributions to prolonging the survival time of patients and improving their quality of life. Among them, the compound of the present invention, as a novel small molecule compound, can attach to the colchicine binding site of tubulin, thereby inhibiting the binding of tubulin. Studies have shown that it can be used in combination with docetaxel to increase efficacy and reduce toxicity, and can exert multiple effects in the tumor microenvironment, including: 1. directly inducing apoptosis of tumor cells by activating Caspase-3; 2. promoting dendritic cell maturation, thereby further promoting T cell-mediated tumor killing; 3. promoting the release of a series of cytokines that protect neutrophils from apoptosis.

Chinese patent application CN106565686 discloses (3Z, 6Z)-3-[((E)-3-(5-tert-butyl)-1H-imidazolyl-4-yl)methylene]-6-((E)-3-(3-fluorophenyl)-2-propenylene) piperazine-2,5-dione, the compound of formula (1). The compound is used to reduce vascular proliferation and vascular density, acts on tumor blood vessels, and has an anticancer effect.

Formula (1)

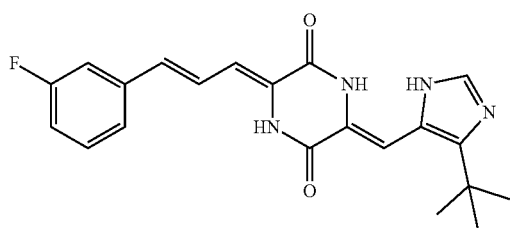

SUMMARY OF THE INVENTION

An object of the present invention is to provide a new crystal form of the above compound, namely crystal form B of (3Z,6Z)-3-[((E)-3-(5-tert-butyl)-1H-imidazolyl-4-yl)methylene]-6-((E)-3-(3-fluorophenyl)-2-propenylene)piperazine-2,5-dione (as shown in formula (1));

Formula (1)

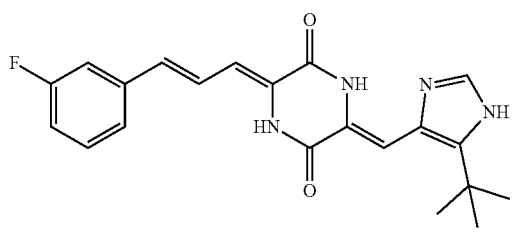

The crystal form B is characterized by melting point, X-ray powder diffraction (XRD), differential scanning calorimetry (DSC), thermogravimetric analysis (TG), infrared spectroscopy (IR), and elemental analysis. The crystal form has the properties required for the preparation of pharmaceutical preparations.

Another object of the present invention is to provide a method of preparing the new crystal form of the compound.

Yet another object of the present invention is to provide a pharmaceutical composition comprising the crystal form of the compound.

According to one aspect of the present invention, crude product of the compound (as shown in formula (1)) is first prepared, and then the crude product is crystallized by recrystallization to obtain the crystal form of the compound.

By melting point measurement, X-ray powder diffraction, DSC, TG, IR and elemental analysis of this crystal, it is confirmed that the obtained crystal is a new type of crystal, called crystal form B.

Specifically, when X-ray powder diffraction is performed with a Cu radiation source, the crystal form B indicates characteristic diffraction peaks at 2θ of 5.5±0.2°, 8.7±0.2°, 11.0±0.2°, 13.5±0.2°, 16.0±0.2°, 16.4±0.2°, and the relative intensities (I/I$_0$) of these peaks are greater than or equal to 30%. Furthermore, the X-ray powder diffraction pattern of the crystal may also comprise characteristic diffraction peaks at 2θ° of 18.5±0.2°, 21.9±0.2°, 22.1±0.2°, and the relative intensities of these peaks are greater than or equal to 15% (see FIG. 1).

Wherein "±0.2°" is the allowable measurement error range.

The crystal form B of the present invention can be characterized by X-ray powder diffraction pattern. It is characterized in that its X-ray powder diffraction pattern has the above-mentioned characteristic diffraction peaks represented by 2θ°, as shown in Table 1, and their relative intensities are close to the following values.

TABLE 1

| | Item | | |
|---|---|---|---|
| No. | 2θ° | d (Interplanar distance) | I/I$_0$ (Relative intensity) |
| 1 | 5.5154 | 16.02367 | 34.26% |
| 2 | 8.7125 | 10.14954 | 84.38% |
| 3 | 11.0397 | 8.01470 | 100.00% |
| 4 | 13.4628 | 6.57712 | 33.04% |
| 5 | 15.9929 | 5.54185 | 32.10% |
| 6 | 16.3546 | 5.42010 | 39.56% |
| 7 | 18.5118 | 4.79307 | 15.07% |
| 8 | 21.8768 | 4.06283 | 21.26% |
| 9 | 22.1430 | 4.01459 | 24.50% |

The term "close" herein refers to the uncertainty of measurement value of the relative intensity. Those skilled in the art understand that the uncertainty of the relative intensity is very dependent on the measurement conditions. The relative intensity value may change, for example, within a range of ±25% or preferably within the range of ±10%.

The above-mentioned crystal form B has an X-ray powder diffraction pattern shown in FIG. 1.

The present invention uses differential scanning calorimetry (DSC) technology to characterize the crystal form B (see FIG. 2), wherein the differential scanning calorimetry analysis results show that the test sample has no discernible endothermic or exothermic process in the detection temperature range (20-310° C.).

The present invention uses thermogravimetric analysis technology to characterize the crystal form B (see FIG. 3), wherein the thermogravimetric spectrum (TG) shows a weight loss of 0.87% from room temperature to 326° C., a weight loss of 39.8% from 326° C. to 436° C., a weight loss of 54.48% from 436° C. to 700° C., and a remaining amount of 0.85% at 700° C. This indicates that as the temperature increases, the compound degrades.

The infrared spectrum of the crystal form B of the compound of the present invention is shown in FIG. 4, wherein it comprises relatively strong absorption peaks at 3175, 3060, 3007, 2969, 2905, 1691-1634, 1600, 1579, 1555, 1503, 1491, 1472, 1376, 1277, 956, 810, 775, and 681 $cm^{-1}$.

Element analysis data of crystal form B of the present invention are in agreement with the theoretical values (with difference within ±0.3%), which further confirms that the compound does not co-crystallize with other solvents (see Table 2).

TABLE 2

| Sample No. | Element content (%) | | |
|---|---|---|---|
| | C | H | N |
| 1 | 66.07 | 5.55 | 14.73 |
| Theoretical value | 66.30 | 5.56 | 14.73 |

According to another aspect of the present invention, the method of preparing the crystalline form B comprises: adding the crude product of (3Z,6Z)-3-[((E)-3-(5-tert-butyl)-1H-imidazolyl-4-yl)methylene]-6-((E)-3-(3-fluorophenyl)-2-propenylene) piperazine-2,5-dione into a mixed solvent of C1-C4 alkyl alcohol and C3-C4 alkyl ketone, heating under reflux to achieve dissolution; after the solution is clarified, cooling the solution to precipitate, filtrating, collecting the precipitate, and drying the collected precipitate with air blasts to obtain the crystal form B. The alkyl alcohol is selected from the group consisting of methanol, ethanol, propanol, isopropanol and butanol, preferably ethanol; the ketone is selected from the group consisting of acetone, methyl ethyl ketone and n-butanone, etc., preferably acetone; the volume ratio (V/V) of alcohol to ketone is 5:1~10:1, preferably 8:1; the ratio of the crude product to the solvent is, based on g/ml, 1:5~20 by weight-volume ratio, preferably 1:10. The solution is preferably heated to 40~80° C., more preferably, the mixed solvent of C1-C4 alkyl alcohol and C3-C4 alkyl ketone to 50° C.; according to this embodiment, the precipitation is carried out for 2~8 hours, more preferably 4 hours. The precipitation temperature is 0~40° C., preferably 10~20° C. After the precipitation followed by filtration, the precipitate is dried at temperature 30~60° C., preferably 50° C.

According to yet another aspect of the present invention, a pharmaceutical composition is provided, which comprises the novel crystal form of the compound and optionally a pharmaceutically acceptable carrier and/or excipient.

The pharmaceutical composition can be further formulated into forms for administration according to conventional formulation methods, including oral or parenteral administration forms. In a form available for administration, a therapeutically effective amount of the crystal form B should be included. The so-called "therapeutically effective amount" means that at this dose, the compound of the present invention can improve or alleviate the symptoms of a disease, or can inhibit or block the development of a disease.

Based on experience and considering standard methods and references in the art, those skilled in the art can easily select various carriers and/or excipients and determine their dosage.

According to yet another aspect of the present invention, the crystal form of the present invention may be used alone in the preparation of drugs for the treatment of hyperproliferative diseases, or it may be prepared and acts synergistically in combination with other therapeutic drugs.

The crystal form B of (3Z,6Z)-3-[((E)-3-(5-tert-butyl)-1H-imidazolyl-4-yl) methylene]-6-((E)-3-(3-fluorophenyl)-2-propenylene)piperazine-2,5-dione of the present invention may be used for treatment of hyperproliferative diseases, preferably cancer, including but not limited to non-small cell lung cancer, colorectal cancer, refractory non-small cell lung cancer, pancreatic cancer, ovarian cancer, breast cancer, neuroglioma, brain cancer, or neck cancer.

The compound is a cell cycle inhibitor, may be used as a tumor growth inhibitor or fungal inhibitor, and may be used to treat or prevent related diseases such as cancer, especially non-small cell lung cancer, colorectal cancer, refractory non-small cell lung cancer, ovarian cancer, pancreatic cancer, breast cancer, neuroglioma, brain tumor or neck cancer.

Beneficial Effect:

The new crystal form of (3Z,6Z)-3-[((E)-3-(5-tert-butyl)-1H-imidazolyl-4-yl) methylene]-6-((E)-3-(3-fluorophenyl)-2-propenylene)piperazine-2,5-dione obtained by the present invention has a stable morphology, good chemical stability, and high temperature resistance. This new crystal form of (3Z,6Z)-3-[((E)-3-(5-tert-butyl)-1H-imidazolyl-4-yl)methylene]-6-((E)-3-(3-fluorophenyl)-2-propenylene)piperazine-2,5-dione possesses the properties necessary for preparation of the formulation, and is easy to store. Its production operation is simpler, and the quality is easier to control.

DETAILED DESCRIPTION OF THE INVENTION

All raw materials and reagents are purchased commercially.

Crude Product Preparation:

The crude product of (3Z,6Z)-3-[((E)-3-(5-tert-butyl)-1H-imidazolyl-4-yl) meth ylene]-6-((E)-3-(3-fluorophenyl)-2-propenylene)piperazine-2,5-dione was prepared using 1,4-diacetylpiperazine-2,5-dione, 5-tert-butyl-1H-imidazole-4-carbaldehyde as starting materials, by referring to the method of the patent publication (CN 106565686).

Example 1

200 g of crude product of (3Z,6Z)-3-[((E)-3-(5-tert-butyl)-1H-imidazolyl-4-yl) methylene]-6-((E)-3-(3-fluorophenyl)-2-propenylene)piperazine-2,5-dione was added to a reaction flask, added with 2000 ml of mixed solvent of ethanol and acetone (V/V=8:1), heated to reflux at 50° C. under stirring. After the crude product was dissolved, the solution was stirred for 10 min, cooled to 20~25° C. to precipitate, and then stirred for 4 hours for crystallization, and filtrated. The filter cake was leached with acetone, and then dried with air blasts at 50° C. with assistance of phosphorus pentoxide. 182 g off-white solid was obtained with a yield of 91.0%, the water content of which was found to be 0.1% by Karl Fischer titrator. The obtained compound was crystal form B of (3Z,6Z)-3-[((E)-3-(5-tert-butyl)-1H-imidazolyl-4-yl)methylene]-6-((E)-3-(3-fluorophenyl)-2-propenylene)piperazine-2,5-dione.

Figure 1:
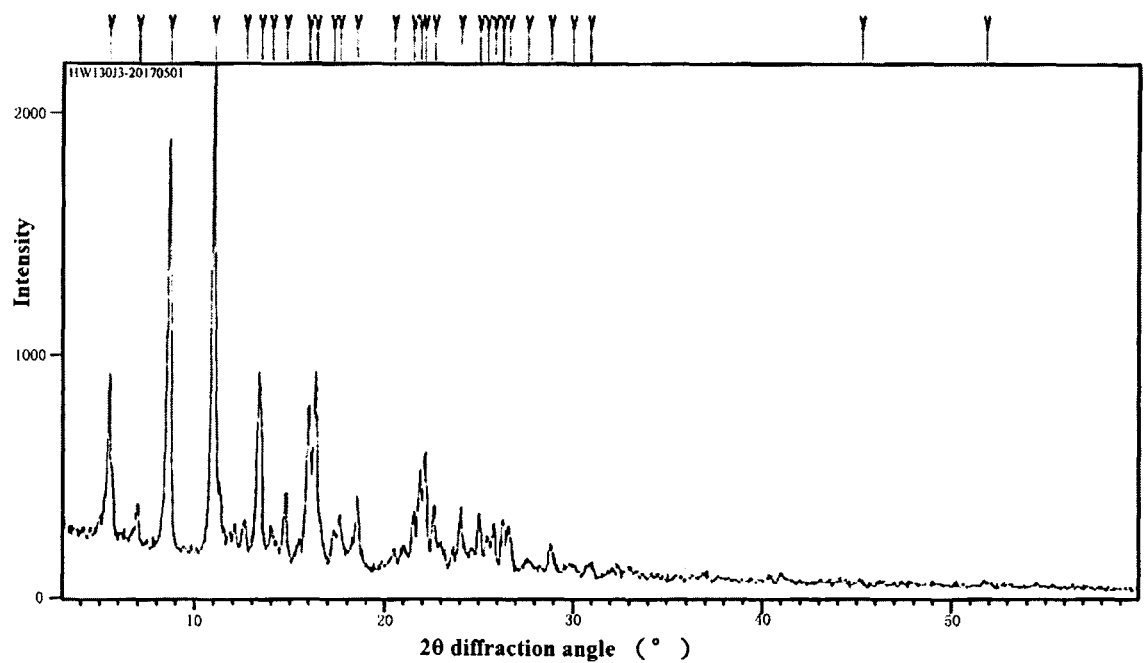
FIG. 1 is an X-ray diffraction pattern of the new crystal form B obtained in Example 1 of the present invention.
Figure 2:
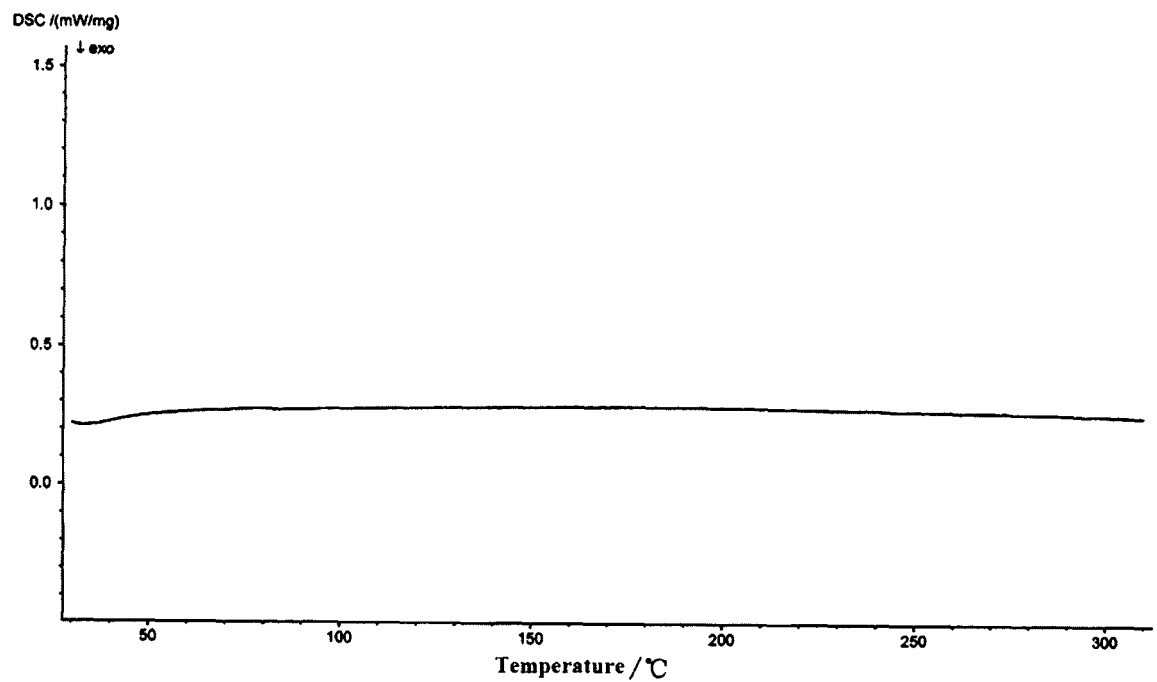
FIG. 2 is a DSC pattern of the new crystal form B obtained in Example 1 of the present invention.
Figure 3:
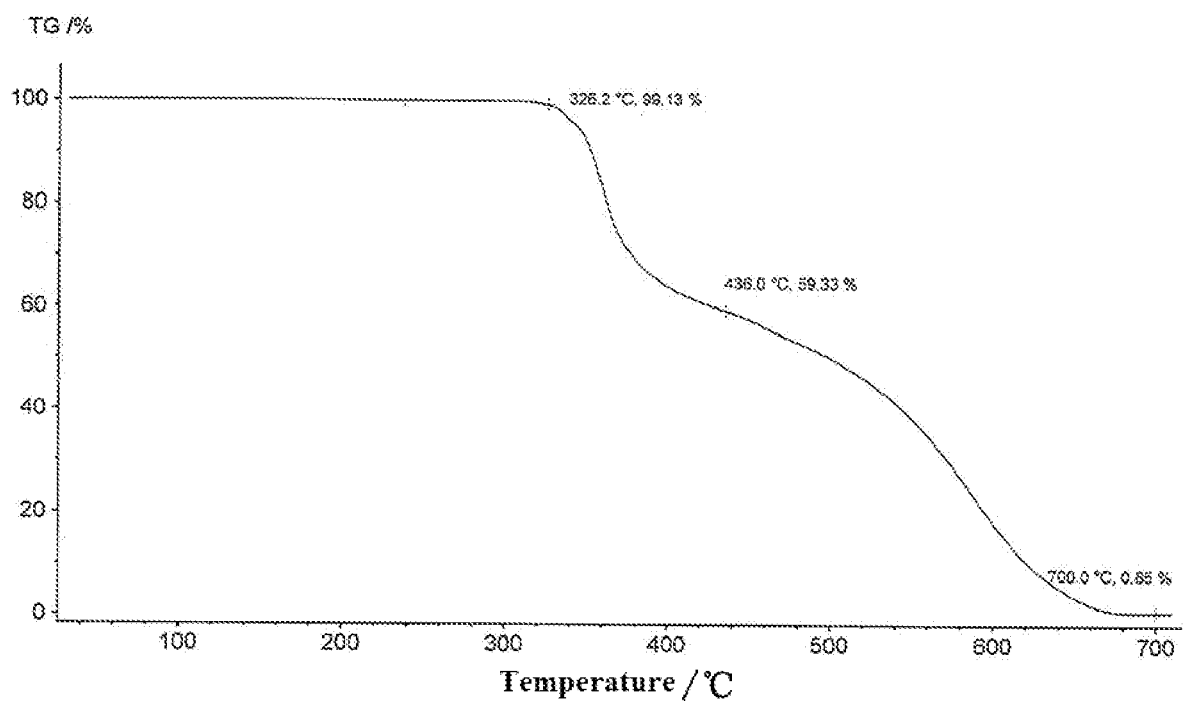
FIG. 3 is a TG pattern of the new crystal form B obtained in Example 1 of the present invention.
Figure 4:
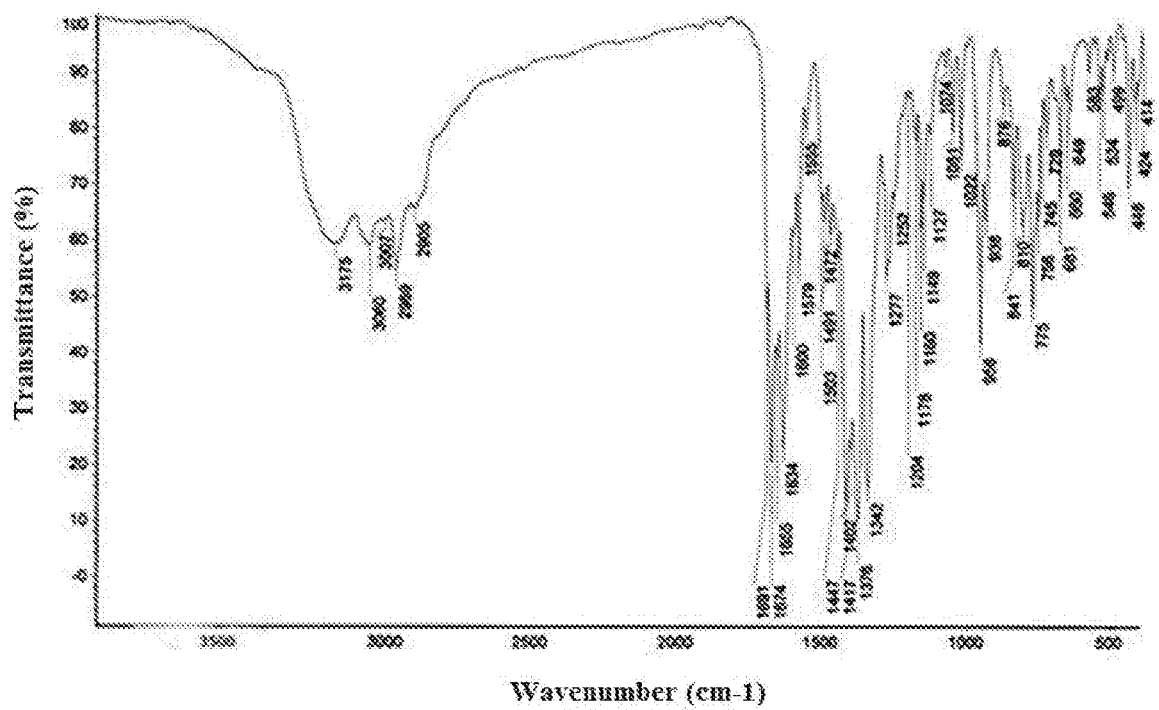
FIG. 4 is an IR spectrum of the new crystal form B obtained in Example 1 of the present invention.
Figure 5:
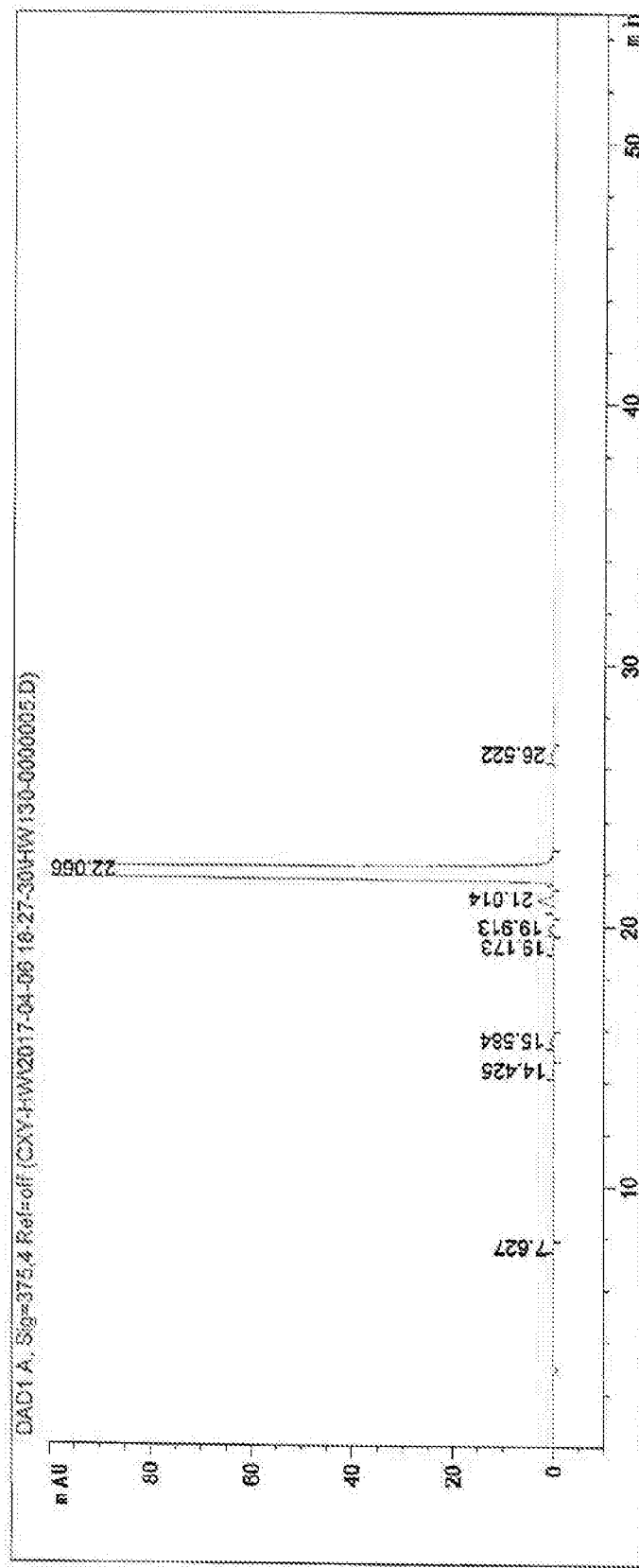
FIG. 5 is a HPLC chromatogram of the new crystal form B obtained in Example 1 of the present invention.

The characteristics of the compound were identified as shown in FIGS. 1 to 5.

Test conditions for the samples of the example:
(1) XRD:
Detection instrument: Empyrean X-ray diffractometer
Detection conditions: Cu target Kα ray, Voltage 40 kV, Current 40 mA, Divergence slit 1/32°, Anti-scatter slit 1/16°, Anti-scatter slit 7.5 mm, 2θ range: 3°-50°, Step size 0.02°, counting time: 40 s/step
Detection basis: 0451 X-ray powder diffraction method, Pharmacopoeia of the People's Republic of China (2015 Edition, Part IV)
Detection results: see FIG. 1.
(2) DSC:
Detection instrument: DSC 204F1 differential scanning calorimeter, NETZSCH Company, Germany
Detection conditions: Atmosphere: $N_2$, 40 ml/min
Scanning procedures: The temperature curve was recorded by heating from room temperature to 250° C. at a rate of 10° C./min
Detected sample quality: Sample 1: 2.48 mg (Aluminum sample tray)
Detection basis: General rules for thermal analysis JY/T 014-1996
Detection results: see FIG. 2.

(3) TG:
Detection instrument: TG209 thermal gravimetric analyzer, NETZSCH company, Germany
Detection condition: Atmosphere: air, 20 ml/min; scanning procedures: room temperature~800° C., heating rate: 10° C./min
Detection basis: General rules for thermal analysis JY/T 014-1996
Detection results: see FIG. 3.
Infrared Spectrum:
Detection instrument: FT-IR NICOLET6700 (U.S.)
Detection condition: potassium bromide disc
Detection basis: General rules for infrared analysis GB/T 6040~2002
Detection results: see FIG. 4.
HPLC
Detection instrument: Agilent 1260 series (U.S.)
Detection Conditions:
Chromatographic column: Waters Sunfire C18;
Mobile phase A: water-mobile phase acetonitrile B (80: 20);
Column temperature: 40° C.; Detection wavelength: 390 nm.
Detection basis: High performance liquid chromatography method, Pharmacopoeia of the People's Republic of China, Part II Appendix VD
Detection results: see FIG. 5.

Example 2

20 g of crude product of (3Z,6Z)-3-[((E)-3-(5-tert-butyl)-1H-imidazolyl-4-yl) methylene]-6-((E)-3-(3-fluorophenyl)-2-propenylene)piperazine-2,5-dione was added into each reaction flask, to carry out the experiments with reference to the experiment operations of Example 1:

TABLE 3

| No. | Organic solvent | Solvent (V/V) | Crude product/ mixed solvent (g/ml) | Heating temp. (° C.) | Precipitation temp. (° C.) | Precipitation time (h) | Drying temp. (° C.) | Yield (%) |
|---|---|---|---|---|---|---|---|---|
| 2 | Methanol/Acetone | 5:1 | 1 g:5 ml | 50 | 0~10 | 2 | 45 | 63 |
| 3 | Methanol/Acetone | 8:1 | 1 g:12 ml | 70 | 10~20 | 4 | 30 | 71 |
| 4 | Methanol/Acetone | 10:1 | 1 g:20 ml | 80 | 20~30 | 8 | 60 | 52 |
| 5 | Methanol/n-butanone | 6:1 | 1 g:6 ml | 55 | 0~10 | 3 | 30 | 45 |
| 6 | Methanol/n-butanone | 8:1 | 1 g:9 ml | 65 | 20~30 | 6 | 50 | 54 |
| 7 | Methanol/n-butanone | 9:1 | 1 g:18ml | 75 | 30~40 | 7 | 60 | 43 |
| 8 | Methanol/methyl ethyl ketone | 7:1 | 1 g:5 ml | 40 | 0~10 | 2 | 30 | 38 |
| 9 | Methanol/methyl ethyl ketone | 8:1 | 1 g:10 ml | 50 | 10~20 | 4 | 50 | 53 |
| 10 | Methanol/methyl ethyl ketone | 10:1 | 1 g:20 ml | 80 | 20~30 | 5 | 55 | 47 |
| 11 | Ethanol/acetone | 5:1 | 1 g:5 ml | 50 | 0~10 | 2 | 45 | 79 |
| 12 | Ethanol/acetone | 10:1 | 1 g:20 ml | 80 | 20~30 | 8 | 60 | 68 |
| 13 | Ethanol/n-butanone | 6:1 | 1 g:6 ml | 55 | 0~10 | 3 | 30 | 56 |
| 14 | Ethanol/n-butanone | 8:1 | 1 g:9 ml | 65 | 20~30 | 6 | 50 | 66 |
| 15 | Ethanol/n-butanone | 9:1 | 1 g:18 ml | 75 | 30~40 | 7 | 60 | 54 |
| 16 | Ethanol/methyl ethyl ketone | 7:1 | 1 g:5 ml | 40 | 0~10 | 2 | 30 | 50 |
| 17 | Ethanol/methyl ethyl ketone | 8:1 | 1 g:10 ml | 50 | 10~20 | 4 | 50 | 59 |
| 18 | Ethanol/methyl ethyl ketone | 10:1 | 1 g:20 ml | 80 | 20~30 | 5 | 55 | 55 |
| 19 | Isopropanol/acetone | 5:1 | 1 g:5 ml | 50 | 0~10 | 2 | 45 | 70 |
| 20 | Isopropanol/acetone | 8:1 | 1 g:12 ml | 70 | 10~20 | 4 | 30 | 75 |
| 21 | Isopropanol/acetone | 10:1 | 1 g:20 ml | 80 | 20~30 | 8 | 60 | 64 |
| 22 | Isopropanol/ n-butanone | 6:1 | 1 g:6 ml | 55 | 0~10 | 3 | 30 | 43 |
| 23 | Isopropanol/ n-butanone | 8:1 | 1 g:9 ml | 65 | 20~30 | 6 | 50 | 51 |
| 24 | Isopropanol/ n-butanone | 9:1 | 1 g:18 ml | 75 | 30~40 | 7 | 60 | 49 |
| 25 | Isopropanol/methyl ethyl ketone | 7:1 | 1 g:5 ml | 40 | 0~10 | 2 | 30 | 40 |

TABLE 3-continued

| No. | Organic solvent | Solvent (V/V) | Crude product/ mixed solvent (g/ml) | Heating temp. (° C.) | Precipitation temp. (° C.) | Precipitation time (h) | Drying temp. (° C.) | Yield (%) |
|---|---|---|---|---|---|---|---|---|
| 26 | Isopropanol/methyl ethyl ketone | 8:1 | 1 g:10 ml | 50 | 10~20 | 4 | 50 | 56 |
| 27 | Isopropanol/methyl ethyl ketone | 10:1 | 1 g:20 ml | 80 | 20~30 | 5 | 55 | 50 |
| 28 | Butanol/acetone | 5:1 | 1 g:5 ml | 50 | 0~10 | 2 | 45 | 42 |
| 29 | Butanol/acetone | 8:1 | 1 g:12 ml | 70 | 10~20 | 4 | 30 | 51 |
| 30 | Butanol/acetone | 10:1 | 1 g:20 ml | 80 | 20~30 | 8 | 60 | 36 |
| 31 | Butanol/n-butanone | 6:1 | 1 g:6 ml | 55 | 0~10 | 3 | 30 | 41 |
| 32 | Butanol/n-butanone | 8:1 | 1 g:9 ml | 65 | 20~30 | 6 | 50 | 48 |
| 33 | Butanol/n-butanone | 9:1 | 1 g:18 ml | 75 | 30~40 | 7 | 60 | 44 |
| 34 | Butanol/methyl ethyl ketone | 7:1 | 1 g:5 ml | 40 | 0~10 | 2 | 30 | 35 |
| 35 | Butanol/methyl ethyl ketone | 8:1 | 1 g:10 ml | 50 | 10~20 | 4 | 50 | 47 |
| 36 | Butanol/methyl ethyl ketone | 10:1 | 1 g:20 ml | 80 | 20~30 | 5 | 55 | 38 |

Experimental conclusions: The alcohol solvent used in the experiment is preferably ethanol; the ketone solvent used in the experiment is preferably acetone; the volume ratio of alcohol to ketone (V/V) is 5:1~10:1, preferably 8:1; the ratio of the crude product to the solvent is, based on g/ml, 1:5~20 by weight to volume ratio, preferably 1:10. The solution is preferably heated to 40~80° C., preferably a mixed solvent of alkyl alcohol and alkyl ketone is heated to 50° C. According to this embodiment, the precipitation is carried out for 2~8 hours, preferably 4 hours. The precipitation temperature is 0~40° C., preferably 10~20° C. After precipitation followed by filtration, the precipitate is dried at temperature 30-60° C., preferably 50° C.

Example 3

Stability Studies on Crystal Form B of (3Z,6Z)-3-[((E)-3-(5-tert-butyl)-1H-imidazolyl-4-yl)methylene]-6-((E)-3-(3-fluorophenyl)-2-propenylene)piperazine-2,5-dione The obtained crystal form B was subjected to stability studies (accelerated test for 10 days), to compare the data of purity, maximum single impurity and total impurities of the new crystal form under the conditions of 60° C., humidity 92.5%, and light irradiation with the data on day 0. The results show that the purity of the obtained crystal form was slightly reduced under the conditions of light irradiation, but stable under other conditions.

TABLE 4

Results of stress testing on crystal form B

Stress testing on crystal form B Sample No. 1 (prepared in Example 1)

| | No. | Purity (%) | Maximum single impurity (%) | Total impurities (%) |
|---|---|---|---|---|
| Day 0 | 1 | 99.50 | 0.24 (RRT: 0.95) | 0.50 |
| Day 5 | 1-60° C. | 99.50 | 0.24 (RRT: 0.95) | 0.50 |
| | 1-92.5% | 99.50 | 0.24 (RRT: 0.95) | 0.50 |
| | 1-light irradiation | 99.40 | 0.26 (RRT: 0.95) | 0.60 |
| Day 10 | 1 | 99.50 | 0.24 (RRT: 0.95) | 0.50 |
| | 1-60° C. | 99.50 | 0.24 (RRT: 0.95) | 0.50 |
| | 1-92.5% | 99.50 | 0.24 (RRT: 0.95) | 0.50 |
| | 1-light irradiation | 99.40 | 0.26 (RRT: 0.95) | 0.60 |

The crude product of (3Z,6Z)-3-[((E)-3-(5-tert-butyl)-1H-imidazolyl-4-yl)methylene]-6-((E)-3-(3-fluorophenyl)-2-propenylene)piperazine-2,5-dione was subjected to stability studies (accelerated test for 10 days), to compare the data of purity, maximum single impurity of the crude product stored at 40° C., 60° C. to the data on day 0. The purities of the crude product stored at 60° C. on day 5 and at 60° C. on day were lower than that of the crystal form B under the same conditions.

TABLE 5

Results of stress testing on crude product

| Sample | Study condition | Content (%) | Maximum single impurity (%) |
|---|---|---|---|
| Crude product, Sample No. 2 | Day 0 | 99.49 | 0.24(RRT: 0.95) |
| | 60° C. Day 5 | 96.89 | 1.14(RRT: 0.91) |
| | 40° C. Day 5 | 99.08 | 0.25(RRT: 0.95) |
| | 60° C. Day 10 | 95.27 | 1.88(RRT: 0.91) |
| | 40° C. Day 10 | 98.68 | 0.50(RRT: 0.95) |

Example 4

Preparation of Injection of Crystal Form B of the Compound

TABLE 6

Formulation 1

| Ingredient | Amount |
|---|---|
| Crystal form B of compound (Example 1) | 20 g |
| Polysorbate-80 | 520 g |
| Hydrochloric acid | proper amount |
| Totally prepared into | 1000 vials |

Preparation Method:

Polysorbate-80 was added with 0.5% dried activated carbon for refinement of injection, heated to 40~60° C., stirred at a constant temperature for 30~60 min, heating filtered until the clarity and color inspections were qualified.

The formulated amount of polysorbate-80 was added dropwise with 13% hydrochloric acid solution under stirring until the measured pH value in the range of 3.5-3.9. Compound B was added and broke up by stirring. The solution was subjected to positive pressure filtration through micropore membrane until the solution was clear, and then the content and pH were tested. After passing the test, the solution was filled in antibiotic tube-type bottles under sterile conditions, 0.5 ml per bottle (including compound B), then filled with nitrogen, stoppered, capped to obtain the products.

Medicinal ethanol was distilled on a water bath, wherein the initial fraction was discarded and the condensate was collected. 195 g of the condensate was weighed, added with injection water to 1500 g, added with 0.3% activated carbon for refinement of injection, heated to reflux for 30 min, cooled, decarbonized, filtered through a 0.22 um micro porous filter membrane until the solution was clear, filled in antibiotic tube-type bottles under class 100 clean conditions, 1.5 ml per bottle; stoppered, capped to obtain the products.

Example 5

The effects of adding no acid, adding different acids in the formulation, as well as different processes (with and without Nitrogen) of the same formulation for the stability of this product were compared. Various indicators were detected and compared on day 7 and day 0, and the results are presented in Table 7. It can be seen from Table 7 that, when there was no acid added in Formulation 3 of the product, related substances increased significantly after 7 days at 40° C. and the crystal B compound content decreased, but other indicators did not change significantly. The formulations having 13% hydrochloric acid (Formulation 2) or 50% citric acid (Formulation 4) were significantly better than the formulation without added acid (Formulation 3), and the formulation in which pH was adjusted with 13% hydrochloric acid was better than the formulation in which pH was adjusted with 50% citric acid. For the same Formulation prepared with different processes, after 7 days at 40° C., the content and related substances of the sample filled with nitrogen did not change much, while the content of the sample without nitrogen decreased and the related substances increased significantly. The sample filled with nitrogen had better stability than the sample without nitrogen. Therefore, the production process of Formulation 1 was selected.

While the description above refers to the preferred embodiments of the invention, various changes or modifications may be made by those skilled in the art without departing from the spirit of the invention, and should belong to the scope of the appended claims of the present invention.

What is claimed is:

1. A crystal form of (3Z,6Z)-3-[((E)-3-(5-tert-butyl)-1H-imidazolyl-4-yl)methylene]-6-((E)-3-(3-fluorophenyl)-2-propenylene)piperazine-2,5-dione represented by Formula (1), characterized in that, the crystal form has an X-ray powder diffraction pattern with characteristic diffraction peaks at 2θ° of 5.5±0.2°, 8.7±0.2°, 11.0±0.2°, 13.5±0.2°, 16.0±0.2°, 16.4±0.2°, 18.5±0.2°, 21.9±0.2° and 22.1±0.2°, (1)

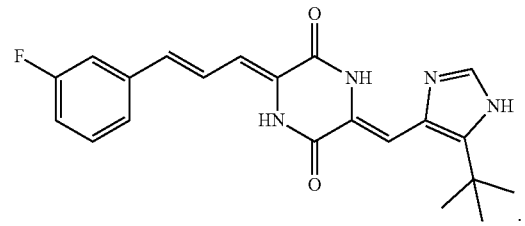

2. The crystal form of (3Z,6Z)-3-[((E)-3-(5-tert-butyl)-1H-imidazolyl-4-yl) methylene]-6-((E)-3-(3-fluorophenyl)-2-propenylene)piperazine-2,5-dione of claim 1, characterized in that, the characteristic diffraction peaks indicate relative intensity $I/I_0$ value as shown in Table 1, and the relative intensity $I/I_0$ value changes in the range of ±25%,

TABLE 1

| | | Item | |
|---|---|---|---|
| No. | 2θ° | d(Interplanar distance) | $I/I_0$(Relative intensity) |
| 1 | 5.5154 | 16.02367 | 34.26% |
| 2 | 8.7125 | 10.14954 | 84.38% |
| 3 | 11.0397 | 8.01470 | 100.00% |
| 4 | 13.4628 | 6.57712 | 33.04% |
| 5 | 15.9929 | 5.54185 | 32.10% |
| 6 | 16.3546 | 5.42010 | 39.56% |

TABLE 7

| Formualtion | Formualtion 1 (with Nitrogen) | Formualtion 2 (without Nitrogen) | Formualtion 3 | Formualtion 4 |
|---|---|---|---|---|
| Crystal form B of the compound | 20 | 20 | 20 | 20 |
| Polysorbate-80 | 520 | 520 | 520 | 520 |
| 13% hydrochloric acid solution | Proper amount | Proper amount | | |
| 50% citric acid solution | | | | Proper amount |
| Day 0 pH value* | 3.70 | 3.70 | 6.18 | 4.54 |
| Labelled amount (%) | 99.85 | 99.85 | 98.40 | 99.21 |
| Related substance (%) | 1.00 | 1.00 | 1.74 | 1.06 |
| Colour | <Y2** | <Y2 | <Y2 | <Y2 |
| Clarity | Clear | Clear | Clear | Clear |
| 40° C. pH value | 3.70 | 3.65 | 6.13 | 4.49 |
| Day 7 Labelled amount (%) | 98.79 | 96.36 | 95.57 | 97.27 |
| Related substance (%) | 1.64 | 3.04 | 4.31 | 2.26 |
| Colour | <Y2 | <Y2 | <Y2 | <Y2 |
| Clarity | Clear | Clear | Clear | Clear |

Note:
*pH measurement method: 0.5 g of the product was added with 4.5 ml water, stirred for 15 minutes, and the pH value was measured according to the method of Chinese Pharmacopoeia (2015 edition), by inserting the electrode followed by stirring for 15 minutes.
Y2: indicates standard colorimetric solution Yellow No. 2 (compliant with the Chinese Pharmacopoeia 2015 edition, supervised by Shanghai Drug Inspection Institute).

TABLE 1-continued

| No. | 2θ° | d(Interplanar distance) | I/I₀(Relative intensity) |
|---|---|---|---|
| 7 | 18.5118 | 4.79307 | 15.07% |
| 8 | 21.8768 | 4.06283 | 21.26% |
| 9 | 22.1430 | 4.01459 | 24.50% |

3. The crystal form of (3Z,6Z)-3-[((E)-3-(5-tert-butyl)-1H-imidazoyl-4-yl) methylene]-6-((E)-3-(3-fluorophenyl)-2-propenylene)piperazine-2,5-dione of claim 2, characterized in that, the relative intensity I/I₀ value changes in the range of ±10%.

4. The crystal form of (3Z,6Z)-3-[((E)-3-(5-tert-butyl)-1H-imidazolyl-4-yl) methylene]-6-((E)-3-(3-fluorophenyl)-2-propenylene)piperazine-2,5-dione of any one of claims 1-3, characterized in that, the crystal form has a thermogravimetric pattern showing a weight loss of 0.87% from room temperature to 326° C., a weight loss of 39.8% from 326° C. to 436° C., a weight loss of 54.48% from 436° C. to 700° C., and a remaining amount of 0.85% at 700° C.

5. The crystal form of (3Z,6Z)-3-[((E)-3-(5-tert-butyl)-1H-imidazolyl-4-yl) methylene]-6-((E)-3-(3-fluorophenyl)-2-propenylene)piperazine-2,5-dione of any one of claims 1-3, characterized in that, the crystal form has an infrared absorption spectrum measured using a potassium bromide disc, showing absorption peaks at 3175, 3060, 3007, 2969, 2905, 1691-1634, 1600, 1579, 1555, 1503, 1491, 1472, 1376, 1277, 956, 810, 775, 681 cm$^{-1}$.

6. A method of preparing the crystal form of (3Z,6Z)-3-[((E)-3-(5-tert-butyl)-1H-imidazolyl-4-yl)methylene]-6-((E)-3-(3-fluorophenyl)-2-propenylene)piperazine-2,5-dione of claim 1, comprising the following steps of:
1) adding crude product of (3Z,6Z)-3-[((E)-3-(5-tert-butyl)-1H-imidazolyl-4-yl) methylene]-6-((E)-3-(3-fluorophenyl)-2-propenylene)piperazine-2,5-dione into a mixed solvent of C1-C4 alkyl alcohol and C3-C4 alkyl ketone, heating under reflux to achieve dissolution;
wherein the alkyl alcohol is selected from the group consisting of methanol, ethanol, propanol, isopropanol and butanol;
the alkyl ketone is selected from the group consisting of acetone, methyl ethyl ketone and n-butanone, and the volume ratio of the alkyl alcohol to the alkyl ketone is 5:1~10:1;
the ratio of the crude product to the solvent, based on g/ml, is 1:5~20 by weight volume ratio, and the heating temperature is 40~80° C.;
2) after the solution is clarified, cooling it to precipitate, filtrating, collecting the precipitate, and drying the collected precipitate with air blasts to obtain the crystal form;
wherein the precipitation is carried out for 2~8 hours, the precipitation temperature is 0~40° C.; after the precipitation followed by filtration, the precipitate is dried at temperature 30~60° C.

7. The preparation method of claim 6, characterized in that,
in the step 1), the alkyl alcohol is ethanol, the alkyl ketone is acetone, and the volume ratio of ethanol to acetone is 8:1;
the ratio of the crude product to the solvent, based on g/ml, is 1:10 by weight to volume ratio, and the heating temperature is 50° C.;
in the step 2), the precipitation is carried out for 4 hours, the precipitation temperature is 10~20° C., and the drying temperature is 50° C.

8. A pharmaceutical composition comprising the crystal form of (3Z,6Z)-3-[((E)-3-(5-tert-butyl)-1H-imidazolyl-4-yl)methylene]-6-((E)-3-(3-fluorophenyl)-2-propenylene)piperazine-2,5-dione of claim 1.

* * * * *